United States Patent [19]
Bird et al.

[11] Patent Number: 5,304,478
[45] Date of Patent: Apr. 19, 1994

[54] MODIFICATION OF CAROTENOID PRODUCTION IN TOMATOES USING PTOM5

[75] Inventors: Colin R. Bird, Berkshire; Donald Grierson, Loughbrough; Wolfgang W. Schuch, Crowthorne, all of England

[73] Assignee: Imperial Chemical Industries PLC, London, England

[21] Appl. No.: 995,950

[22] Filed: Dec. 28, 1992

Related U.S. Application Data

[63] Continuation of Ser. No. 625,664, Dec. 13, 1990, abandoned.

[30] Foreign Application Priority Data

Dec. 13, 1989 [GB] United Kingdom ............... 8928179

[51] Int. Cl.$^5$ ..................... C12N 15/29; C12N 15/22; A01H 4/00
[52] U.S. Cl. ................. 435/172.3; 536/23.6; 800/205; 800/DIG. 44; 800/DIG. 64
[58] Field of Search .......... 435/320.1, 172.3; 935/64, 67; 800/205, 250, DIG. 44, DIG. 64; 536/23.6

[56] References Cited

PUBLICATIONS

Napoli, et al. (Apr. 1990) The Plant Cell 2:279-289.
van der Krol, et al (1990) The Plant Cell 2:291-299.
van der Krol, et al (1990) Plant Molecular Biology 14:457-466.
Mutschler, et al (1988) Theor. Appl. Genet. 76:285-292.
Giovannoni, et al (Jan. 1989) The Plant Cell 1:53-63.
Smith et al (Aug. 1988) Nature 334:724-726.
Ray, et al (1987) Nucleic Acids Research 15(24):10587.

*Primary Examiner*—Che S. Chereskin
*Attorney, Agent, or Firm*—Cushman, Darby & Cushman

[57] ABSTRACT

The gene of the construct pTOM5 is involved in the carotenoid pathway, which produces carotenes, lutein, xanthophylls, and pigments such as lycopene. The invention proposes to modify (inhibit or promote) the synthesis of such compounds in plants using novel DNA constructs comprising a DNA sequence homologous to some or all of the gene encoded by the clone pTOM5, preceded by a plant promoter. In particular, colour of plant parts, especially fruit, may be modified. Yellow tomatoes are disclosed.

6 Claims, 8 Drawing Sheets

FIG. 1

SEQ ID NO: 1
SEQUENCE TYPE: Nucleotide
SEQUENCE LENGTH: 1646 base pairs

STRANDEDNESS: single
TOPOLOGY: linear
MOLECULE TYPE: cDNA

ORIGINAL SOURCE ORGANISM: Tomato var. Ailsa Craig
IMMEDIATE EXPERIMENTAL SOURCE: Ripe fruit cDNA library FEATURES:
from 201 to 1436 bp  open reading frame PROPERTIES: cDNA of tomato fruit ripening related gene - pTOM5

```
TTTGCCTGTC TGTGGTCTTT TTATAATCTT TTTCTACAGA AGAGAAAGTG GGTAATTTTG   60
TTTGAGAGTG GAAATATTCT CTAGTGGGAA TCTACTAGGA GTAATTTATT TTCTATAAAC  120
TAAGTAAAGT TTGGAAGGTG ACAAAAAGAA AGACAAAAAT CTTGGAATTG TTTTAGACAA  180
CCAAGGTTTT CTTGCTCAGA ATGTCTGTTG CCTTGTTATG GGTTGTTTCT CCTTGTGACG  240
TCTCAAATGG GACAAGTTTC ATGGAATCAG TCCGGGAGGG AAACCGTTTT TTTGATTCAT  300
CGAGGCATAG GAATTTGGTG TCCAATGAGA GAATCAATAG AGGTGGTGGA AAGCAAACTA  360
ATAATGGACG GAAATTTTCT GTACGGTCTG CTATTTTGGC TACTCCATCT GGAGAACGGA  420
CGATGACATC GGAACAGATG GTCTATGATG TGGTTTTGAG GCAGGCAGCC TTGGTGAAGA  480
GGCAACTGAG ATCTACCAAT GAGTTAGAAG TGAAGCCGGA TATACCTATT CCGGGGAATT  540
TGGGCTTGTT GAGTGAAGCA TATGATAGGT GTGGTGAAGT ATGTGCAGAG TATGCAAAGA  600
CGTTTAACTT AGGAACTATG CTAATGACTC CCGAGAGAAG AAGGGCTATC TGGGCAATAT  660
ATGTATGGTG CAGAAGAACA GATGAACTTG TTGATGGCCC AAACGCATCA TATATTACCC  720
CGGCAGCCTT AGATAGGTGG GAAAATAGGC TAGAAGATGT TTTCAATGGG CGGCCATTTG  780
ACATGCTCGA TGGTGCTTTG TCCGATACAG TTTCTAACTT TCCAGTTGAT ATTCAGCCAT  840
TCAGAGATAT GATTGAAGGA ATGCGTATGG ACTTGAGAAA ATCGAGATAC AAAAACTTCG  900
ACGAACTATA CCTTTATTGT TATTATGTTG CTGGTACGGT TGGGTTGATG AGTGTTCCAA  960
TTATGGGTAT CGCCCCTGAA TCAAAGGCAA CAACAGAGAG CGTATATAAT GCTGCTTTGG 1020
CTCTGGGGAT CGCAAATCAA TTAACTAACA TACTCAGAGA TGTTGGAGAA GATGCCAGAA 1080
GAGGAAGAGT CTACTTGCCT CAAGATGAAT TAGCACAGGC AGGTCTATCC GATGAAGATA 1140
TATTTGCTGG AAGGGTGACC GATAAATGGA GAATCTTTAT GAAGAAACAA ATACATAGGG 1200
CAAGAAAGTT CTTTGATGAG GCAGAGAAAG GCGTGACAGA ATTGAGCTCA GCTAGTAGAT 1260
TCCCTGTATG GGCATCTTTG GTCTTGTACC GCAAAATACT AGATGAGATT GAAGCCAATG 1320
ACTACAACAA CTTCACAAAG AGAGCATATG TGAGCAAATC AAAGCAAGTT GATTGCATTA 1380
CCTATTGCAT ATGCAAAATC TCTTGTGCCT CCTACAAAAC TGCCTCTCTT CAAAGATAAA 1440
GCATGAAATG AAGATATATA TATATATATA TATAGCAATG TACATTAGAA GAAAAAAAGG 1500
AAGAAGAAAT GTTGTTGTAT TGATATAAAT GTATATCATA AATATTAGGT TGTAGTAACA 1560
TTCAATATAA TTATCTCTTG TAGTTGTTGT ATCTTCACTT TATCTCAACT CCTTTGAGAG 1620
AACTTTCCGT AAAAAAAAAA AAAAAA                                     1646
```

FIG. 2
Strategy for synthesis of BamHI-KpnI fragments by PCR from pTOM5

FIG. 3

Oligonucleotides used in PCR reactions with pTOM5 to synthesise BamHI-KpnI fragments for cloning into pJR1

```
Oligo     5'                                                              3'

****
TSAS-1    GGGGGGGGATCCTTTGCCTGTCTGTGGTCTTTTTATAATCTT
              BamHI

***
TSAS-2    GCAAGGGTACCTTGGTTGTCTAAAACAATTCCAAGATTTTTGTC
              KpnI

***
TSAS-3    CGGACAAGGTACCATCGAGCATGTCAAATGGCCGCCCATTG
              KpnI

**  *
TSAS-4    TTTTTTTGGTACCGAAGTCTCTCAAGATAATAAGTGAATACAC
              KpnI
```

\* - base change from pTOM5 sequence

FIG. 4

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 51 base pairs
        ( B ) TYPE: nucleic acid
        ( C ) STRANDEDNESS: single
        ( D ) TOPOLOGY: linear     ( i i ) MOLECULE TYPE: cDNA     ( x i ) SEQUENCE DESCRIPTION: SEQ ID NO:1:

```
CCGTCCCCGT GCATGCCTGC AGGTCGACTC TAGAGGATCT TCAATATATA G                    51
```

( 2 ) INFORMATION FOR SEQ ID NO:2:

( i ) SEQUENCE CHARACTERISTICS:
        ( A ) LENGTH: 1646 base pairs
        ( B ) TYPE: nucleic acid
        ( C ) STRANDEDNESS: single
        ( D ) TOPOLOGY: linear     ( i i ) MOLECULE TYPE: cDNA     ( x i ) SEQUENCE DESCRIPTION: SEQ ID NO:2:

```
TTTGCCTGTC TGTGGTCTTT TTATAATCTT TTTCTACAGA AGAGAAAGTG GGTAATTTTG          60
TTTGAGAGTG GAAATATTCT CTAGTGGGAA TCTACTAGGA GTAATTTATT TTCTATAAAC         120
TAAGTAAAGT TTGGAAGGTG ACAAAAAGAA AGACAAAAAT CTTGGAATTG TTTTAGACAA         180
CCAAGGTTTT CTTGCTCAGA ATGTCTGTTG CCTTGTTATG GGTTGTTTCT CCTTGTGACG         240
TCTCAAATGG GACAAGTTTC ATGGAATCAG TCCGGGAGGG AAACCGTTTT TTTGATTCAT         300
CGAGGCATAG GAATTTGGTG TCCAATGAGA GAATCAATAG AGGTGGTGGA AAGCAAACTA         360
ATAATGGACG GAAATTTTCT GTACGGTCTG CTATTTTGGC TACTCCATCT GGAGAACGGA         420
CGATGACATC GGAACAGATG GTCTATGATG TGGTTTTGAG GCAGGCAGCC TTGGTGAAGA         480
GGCAACTGAG ATCTACCAAT GAGTTAGAAG TGAAGCCGGA TATACCTATT CCGGGGAATT         540
TGGGCTTGTT GAGTGAAGCA TATGATAGGT GTGGTGAAGT ATGTGCAGAG TATGCAAAGA         600
CGTTTAACTT AGGAACTATG CTAATGACTC CCGAGAGAAG AAGGGCTATC TGGGCAATAT         660
ATGTATGGTG CAGAAGAACA GATGAACTTG TTGATGGCCC AAACGCATCA TATATTACCC         720
CGGCAGCCTT AGATAGGTGG GAAAATAGGC TAGAAGATGT TTTCAATGGG CGGCCATTTG         780
ACATGCTCGA TGGTGCTTTG TCCGATACAG TTTCTAACTT TCCAGTTGAT ATTCAGCCAT         840
TCAGAGATAT GATTGAAGGA ATGCGTATGG ACTTGAGAAA ATCGAGATAC AAAAACTTCG         900
ACGAACTATA CCTTTATTGT TATTATGTTG CTGGTACGGT TGGGTTGATG AGTGTTCCAA         960
TTATGGGTAT CGCCCCTGAA TCAAAGGCAA CAACAGAGAG CGTATATAAT GCTGCTTTGG        1020
CTCTGGGGAT CGCAAATCAA TTAACTAACA TACTCAGAGA TGTTGGAGAA GATGCCAGAA        1080
GAGGAAGAGT CTACTTGCCT CAAGATGAAT TAGCACAGGC AGGTCTATCC GATGAAGATA        1140
TATTTGCTGG AAGGGTGACC GATAAATGGA GAATCTTTAT GAAGAAACAA ATACATAGGG        1200
CAAGAAAGTT CTTTGATGAG GCAGAGAAAG GCGTGACAGA ATTGAGCTCA GCTAGTAGAT        1260
TCCCTGTATG GGCATCTTTG GTCTTGTACC GCAAAATACT AGATGAGATT GAAGCCAATG        1320
ACTACAACAA CTTCACAAAG AGAGCATATG TGAGCAAATC AAAGCAAGTT GATTGCATTA        1380
CCTATTGCAT ATGCAAAATC TCTTGTGCCT CCTACAAAAC TGCCTCTCTT CAAAGATAAA        1440
GCATGAAATG AAGATATATA TATATATATA TATAGCAATG TACATTAGAA GAAAAAAGG         1500
AAGAAGAAAT GTTGTTGTAT TGATATAAAT GTATATCATA AATATTAGGT TGTAGTAACA        1560
TTCAATATAA TTATCTCTTG TAGTTGTTGT ATCTTCACTT TATCTCAACT CCTTTGAGAG        1620
AACTTTCCGT AAAAAAAAAA AAAAAA                                             1646
```

( 2 ) INFORMATION FOR SEQ ID NO:3:

( i ) SEQUENCE CHARACTERISTICS:
        ( A ) LENGTH: 41 base pairs
        ( B ) TYPE: nucleic acid
        ( C ) STRANDEDNESS: single
        ( D ) TOPOLOGY: linear     ( i i ) MOLECULE TYPE: cDNA ( x i ) SEQUENCE DESCRIPTION: SEQ ID NO:3:

GGGGGGGATC CTTTGCCTGT CTGTGGTCTT TTTATAATCT T    41

( 2 ) INFORMATION FOR SEQ ID NO:4:

( i ) SEQUENCE CHARACTERISTICS:
        ( A ) LENGTH: 44 base pairs
        ( B ) TYPE: nucleic acid
        ( C ) STRANDEDNESS: single
        ( D ) TOPOLOGY: linear     ( i i ) MOLECULE TYPE: cDNA     ( x i ) SEQUENCE DESCRIPTION: SEQ ID NO:4:

GCAAGGGTAC CTTGGTTGTC TAAAACAATT CCAAGATTTT TGTC    44

( 2 ) INFORMATION FOR SEQ ID NO:5:

( i ) SEQUENCE CHARACTERISTICS:
        ( A ) LENGTH: 41 base pairs
        ( B ) TYPE: nucleic acid
        ( C ) STRANDEDNESS: single
        ( D ) TOPOLOGY: linear     ( i i ) MOLECULE TYPE: cDNA     ( x i ) SEQUENCE DESCRIPTION: SEQ ID NO:5:

CGGACAAGGT ACCATCGAGC ATGTCAAATG GCCGCCCATT G    41

( 2 ) INFORMATION FOR SEQ ID NO:6:

( i ) SEQUENCE CHARACTERISTICS:
        ( A ) LENGTH: 43 base pairs
        ( B ) TYPE: nucleic acid
        ( C ) STRANDEDNESS: single
        ( D ) TOPOLOGY: linear     ( i i ) MOLECULE TYPE: cDNA     ( x i ) SEQUENCE DESCRIPTION: SEQ ID NO:6:

TTTTTTTGGT ACCGAAGTCT CTCAAGATAA TAAGTGAATA CAC    43

MODIFICATION OF CAROTENOID PRODUCTION IN TOMATOES USING PTOM5

This is a continuation of application Ser. No. 07/625,664, filed Dec. 13, 1990, now abandoned.

This application relates to novel DNA constructs, plant cells containing them and plants derived therefrom. In particular it involves the use of recombinant DNA technology to control gene expression in plants.

In work leading to the present invention we have identified a gene which expresses an enzyme involved in the ripening of tomatoes. This gene has been cloned and characterized. We have now shown that it is involved in carotenoid synthesis. The gene in question is encoded (almost completely) in the clone pTOM5, disclosed by Ray et al (Nucleic Acids Research, 15, 10587, 1987).

Figure 4:
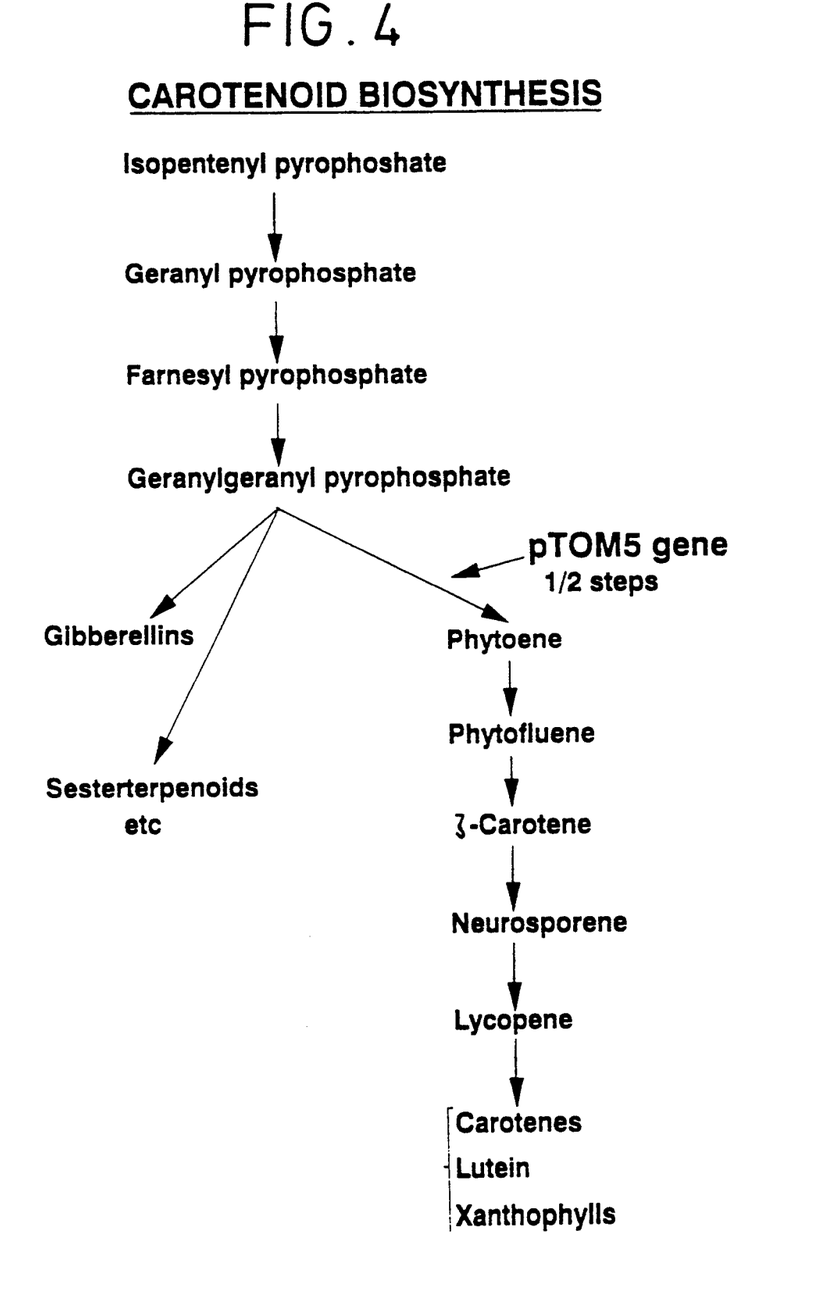
FIG. 4 is a diagram of the carotenoid synthesis pathway.

The carotenoid biosynthesis pathway is shown in outline in FIG. 4 hereof. We believe that the pTOM5 gene is involved in the step or steps of the pathway between geranylgeranyl pyrophosphate and phytoene. Among the products produced by this branch of the pathway are carotenes, lutein, xanthophylls, and pigments such as lycopene. The present invention proposes to modify the synthesis of such compounds in plants.

According to the present invention we provide DNA constructs comprising a DNA sequence homologous to some or all of the gene encoded by the clone pTOM5, preceded by a transcriptional initiation region operative in plants, so that the construct can generate mRNA in plant cells. We further provide a process for modifying the production of carotenoids in plants by transforming such plants with constructs according to the present invention. We further provide a process for modifying the production of carotenoids in plants by transforming such plants with DNA adapted to modify carotenoid biosynthesis and growing such transformed plants or their descendants to produce plant parts (for example leaves, petals or fruit) of modified carotenoid content. Suitable DNA comprises, inter alia, constructs according to the present invention, but other similar constructs affecting other parts of the carotenoid pathway may also be used. Such constructs may be adapted to enhance the production of carotenoids (for example lycopene) or inhibit such production by the plant.

As is well known, a cell manufactures protein by transcribing the DNA of the gene for that protein to produce messenger RNA (mRNA), which is then processed (e.g. by the removal of introns) and finally translated by ribosomes into protein. This process may be inhibited by the presence in the cell of "antisense RNA". By this term is meant an RNA sequence which is complementary to a sequence of bases in the mRNA in question: complementary in the sense that each base (or the majority of bases) in the antisense sequence (read in the 3' to 5' sense) is capable of pairing with the corresponding base (G with C, A with U) in the mRNA sequence read in the 5' to 3' sense. It is believed that this inhibition takes place by formation of a complex between the two complementary strands of RNA, preventing the formation of protein. How this works is uncertain: the complex may interfere with further transcription, processing, transport or translation, or degrade the mRNA, or have more than one of these effects. Such antisense RNA may be produced in the cell by transformation with an appropriate DNA construct arranged to transcribe backwards part of the coding strand (as opposed to the template strand) of the relevant gene (or of a DNA sequence showing substantial homology therewith).

The use of this technology to downregulate the expression of specific plant genes has been described, for example in European Patent publication no 271988 to ICI (corresponding to U.S. Ser. No. 119614). Reduction of gene expression has led to a change in the phenotype of the plant: either at the level of gross visible phenotypic difference e.g. lack of anthocyanin production in flower petals of petunia leading to colourless instead of coloured petals (van der Krol et al, Nature, 333, 866–869, 1988); or at a more subtle biochemical level e.g. change in the amount of polygalacturonase and reduction in depolymerisation of pectins during tomato fruit ripening (Smith et al, Nature, 334, 724–726, 1988; Smith et al., Plant Molecular Biology, 14, 369–379, 1990). Thus antisense RNA has been proven to be useful in achieving downregulation of gene expression in plants.

In a further aspect, the present invention provides DNA constructs comprising a transcriptional initiation region operative in plants positioned for transcription of a DNA sequence encoding RNA complementary to a sequence of bases showing substantial homology to an mRNA encoding the enzyme produced by the gene in pTOM5. The invention also includes plant cells containing constructs according to the invention; plants derived therefrom showing modified characteristics, e.g. fruit colour; and fruit and seeds of such plants.

The constructs of the invention may be inserted into plants to regulate the production of the pTOM5 enzyme. Depending on the nature of the construct, the production of the enzyme may be increased, or reduced, either throughout or at particular stages in the life of the plant. Generally, as would be expected, production of the enzyme is enhanced only by constructs which contain DNA homologous to the substantially complete gene. What is more surprising is that constructs containing an incomplete DNA sequence substantially shorter than that corresponding to the complete gene generally inhibit the expression of the enzyme, whether they are arranged to express sense or antisense RNA.

Further evidence for the function of the pTOM5 gene in the carotenoid pathway (see FIG. 4) is a significant degree of homology (27% identity; 17% similarity) between the polypeptide predicted from the translation of the pTOM5 sequence and the protein encoded by the crtB gene from *Rhodobacter capsulatus*, a gram-negative purple non-sulphur bacterium. The crtB gene product catalyses the tail to tail dimerisation of geranylgeranyl pyrophosphate to form prephytoene pyrophosphate. This enzyme (prephytoene synthetase) is the point of divergence of carotenoid biosynthesis from other isoprenoid metabolism. Further, an enzyme has been isolated from *Capsicum annuum* fruit chromoplasts which is believed to catalyse both the synthesis of prephytoene pyrophosphate and its subsequent conversion to phytoene. This enzyme has a molecular weight of 47,500, in close agreement with the predicted size of the pTOM5 protein (48,000).

As well as colour production, other important functions may be modified by the process of the invention. Thus β-carotene (a precursor of Vitamin A) and other carotenoids are important to human health, and have been claimed to have a protective effect against certain diseases. Food plants may be modified by transformation with the constructs of the invention so that they have a higher content of such compounds: or other plants may be so modified, so that they can act as a source from which such compounds can be extracted. Carotenoids are also believed to have a role in protecting plants against high light intensity damage, so plants with a higher content of such compounds may be of value in combating the effects of any global climate change.

A further possible application of the invention is to control sporopollenin synthesis. This polymer is believed to be a product of carotenoid biosynthesis. Sporopollenin is important during pollen formation and maturation, particularly during the early stages of sporogenesis. Modification of expression of the pTOM5 gene according to the invention in the tapetum is expected to lead to interference in pollen formation, particularly through changing the formation, development or function of the tapetum. Thus inhibition of sporopollenin may be effected in all plants producing sporopollenin through a route involving carotenoids. Accordingly the invention may be used to inhibit the production of pollen in transformed plants. Plants so produced will be male-sterile, and will be useful in the commercial production of uniform hybrids. For this application it is important to use constructs containing promoters which are functional in the tapetum, for example the pollen promoter MFS 14. Not all constitutive promoters work in the tapetum (for example, the CaMV 35S promoter does not).

The plants to which the present invention can be applied include commercially important fruit-bearing plants, in particular the tomato. In this way, plants can be generated which have modified colour due to promotion or inhibition of the pathways of carotenoid biosynthesis (and in particular of the pigment lycopene).

The invention may be used to promote or inhibit the production of the red colour associated with lycopene. Inhibition of this red colour in tomato fruit (eg by transformation with antisense constructs) gives fruit of an attractive shade of yellow (like certain peppers). Similar yellow tomatoes are known, but the present invention provides a means of transferring the trait into elite lines without a prolonged breeding programme which might alter other traits at the same time. Promotion of lycopene production may produce tomato fruit of a deeper red colour, which may appear more appetising to the consumer, particularly in the form of processed material such as pastes and soups. The invention may also be used to introduce a red colour into parts of plants other than the fruit. Promotion of lycopene may be brought about by inserting one or more functional copies of the gene cDNA, or of the full-length gene, under control of a promoter functional in plants. If lycopene is naturally expressed in the plant, the promoter may be selected to give a higher degree of expression than is given by the natural promoter.

Antisense DNA constructs according to the invention may be very short. They preferably comprise a homologous base sequence at least 10 bases in length. There is no theoretical upper limit to the base sequence—it may be as long as the relevant mRNA produced by the cell—but for convenience it will generally be found suitable to use sequences between 100 and 2000 bases in length. The preparation of such constructs is described in more detail below.

The preferred DNA for use in the present invention is DNA derived from the clone pTOM5. The required DNA encoding antisense RNA can be obtained in several ways: by cutting with restriction enzymes an appropriate sequence of such DNA; by synthesizing a DNA fragment using synthetic oligonucleotides which are annealed and then ligated together in such a way as to give suitable restriction sites at each end; by using synthetic oligonucleotides in a polymerase chain reaction (PCR) to generate the required fragment with suitable restriction sites at each end. The DNA is then cloned into a vector containing upstream promoter and downstream terminator sequences, the cloning being carried out so that the DNA sequence is inverted with respect to its orientation in the strand from which it was cut.

In new vectors expressing antisense RNA, the strand that was formerly the template strand becomes the coding strand, and vice versa. The new vector will thus encode RNA in a base sequence which is complementary to the sequence of pTOM5 mRNA. Thus the two RNA strands are complementary not only in their base sequence but also in their orientations (5' to 3').

As source of the DNA base sequence for transcription, it is convenient to use a cDNA clone such as pTOM5. The base sequence of pTOM5 is set out in FIG. 1. This clone has been deposited at the National Collections of Industrial and Marine Bacteria, now at 23 St. Machar Drive, Aberdeen AB21RY, Scotland, as a plasmid in $E.coli$, under the reference NCIB 40191, on Sep. 1, 1989. Alternatively, a cDNA clone similar to pTOM5 may be obtained from the mRNA of ripening tomatoes by the method described by Slater et al, Plant Molecular Biology 5, 137-147, 1985. In this way may be obtained sequences coding for the whole, or substantially the whole, of the mRNA produced by pTOM5. Suitable lengths of the cDNA so obtained may be cut out for use by means of restriction enzymes.

As previously stated, the preferred source of antisense RNA for use in the present invention is DNA showing homology to the gene encoded by the clone pTOM5 (deposited at the NCIMB as 40191, see above). pTOM5 was derived from a cDNA library isolated from ripe tomato RNA (Slater et al Plant Molecular Biology 5, 137-147, 1985). Three other clones (pTOM45, pTOM91, pTOM104) from the same library cross-hybridise to pTOM5 and probably contain related sequences. pTOM5 has been characterized by hybrid select translation to encode a protein of approximately 48kD (Slater et al, Plant Molecular Biology 5, 137-147, 1985). DNA sequence analysis has demonstrated that the clone is 1600 bases long with an open reading frame encoding a polypeptide of 46.7kD.

We have shown that the mRNA for which pTOM5 codes is expressed in ripening tomato fruit. No expression could be detected in green fruit. pTOM5 is expressed most strongly at the full orange stage of ripening. The level of mRNA then declines in line with the general decline in biosynthetic capacity of the ripening fruit. Expression of pTOM5 mRNA could also be induced by exposing mature green fruit to exogenous ethylene. The expression of pTOM5 is reduced in the Ripening inhibitor (rin) and Neverripe (Nr) tomato fruit ripening mutants which mature very slowly, and never achieve the full red colour associated with ordinary tomato fruit.

The genomic locations in the tomato of sequences homologous to pTOM5 have been identified using RFLP mapping: two loci, on chromosome 2 and chromosome 3 respectively, carry sequences homologous to pTOM5. It has also been shown by Southern blotting that the gene may be present as a small multigene family. Genomic clones representing two individual genes have been isolated and characterized by DNA sequence analysis. gTOM5 represents a gene with exon sequence identical to pTOM5. Clone F contains sequence similar, but not identical to pTOM5. Sequence and expression data suggest that Clone F encodes an untranscribed pseudogene.

Although there is a considerable body of information on the structure and expression of the pTOM5 gene family, the biochemical function of this clone has not hitherto been known.

An alternative source of DNA for the base sequence for transcription is a suitable gene encoding the pTOM5 enzyme. This gene may differ from the cDNA of pTOM5 in that introns may be present. The introns are not transcribed into mRNA (or, if so transcribed, are subsequently cut out). When using such a gene as the source of a partial base sequence for transcription it is possible to use either intron or exon regions.

A further way of obtaining a suitable DNA base sequence for transcription is to synthesize it ab initio from the appropriate bases, for example using FIG. 1 as a guide.

Recombinant DNA and vectors according to the present invention may be made as follows. A suitable vector containing the desired base sequence for transcription (for example pTOM5) is treated with restriction enzymes to cut the sequence out. The DNA strand so obtained is cloned (if desired, in reverse orientation) into a second vector containing the desired promoter sequence, for example cauliflower mosaic virus 35S promoter or the tomato polygalacturonase gene promoter sequence—Bird et al., Plant Molecular Biology, 11,651–662, 1988) and the desired terminator sequence (for example the 3' of the Agrobacterium tumefaciens nopaline synthase gene, the nos 3' end).

According to the invention we propose to use both constitutive promoters (such as cauliflower mosaic virus 35S) and inducible or developmentally regulated promoters (such as the ripe-fruit specific polygalacturonase promoter) as circumstances require. Use of a constitutive promoter will tend to affect functions in all parts of the plant: while by using a tissue-specific promoter, functions may be controlled more selectively. Thus in applying the invention, e.g. to tomatoes, it may be found convenient to use the promoter of the PG gene (Bird et al, 1988, cited above). Use of this promoter, at least in tomatoes, has the advantage that the production of recombinant RNA is under the control of a ripening-specific promoter. Thus the recombinant RNA is only produced in the organ in which its action is required. By this means particular organs can have their colour modified. For plants to be used as ornament (as many are), by using a constitutive promoter one may induce carotenoid production throughout the plant to provide plants with an overall modified or reddish/yellowish colour: normally it will be preferred to limit the production to particular sites (such as fruit, flower petals or tubers) by using a tissue-specific or developmentally regulated promoter, for example the PG gene promoter referred to above. Other ripening-specific promoters that could be used include the E8 promoter (Diekman & Fischer, EMBO Journal 7, 3315–3320, 1988) and the 2A11 promoter from tomatoes described in U.S. Pat. No. 4,943,674 to Calgene.

Vectors according to the invention may be used to transform plants as desired, to make plants according to the invention. Dicotyledonous plants, such as tomato, may be transformed by Agrobacterium Ti plasmid technology, for example as described by Bevan (1984) Nucleic Acid Research, 12, 8711–8721. Such transformed plants may be reproduced sexually, or by cell or tissue culture.

The degree of production of RNA in the plant cells can be controlled by suitable choice of promoter sequences, or by selecting the number of copies, or the site of integration, of the DNA sequences according to the invention that are introduced into the plant genome. In this way it may be possible to modify colour formation to a greater or lesser extent.

The constructs of our invention may be used to transform cells of both monocotyledonous and dicotyledonous plants in various ways known to the art. In many cases such plant cells (particularly when they are cells of dicotyledonous plants) may be cultured to regenerate whole plants which subsequently reproduce to give successive generations of genetically modified plants. Examples of genetically modified plants according to the present invention include, as well as tomatoes, fruits of such as mangoes, peaches, apples, pears, strawberries, bananas and melons. The fruit of such plants may be made more attractive (or at least interesting) by inducing or intensifying a red colour therein. Other plants that may be modified by the process of the invention include tubers such as radishes, turnips and potatoes, as well as cereals such as maize (corn), wheat, barley and rice. Flowers of modified colour, and ornamental grasses either red or reddish overall, or having red seedheads, may be produced.

Plants produced by the process of the invention may also contain other recombinant constructs, for example constructs having other effects on fruit ripening. In particular tomatoes of enhanced colour according to the invention may also contain constructs inhibiting the production of enzymes such as polygalacturonase and pectinesterase, or interfering with ethylene production (eg from pTOM13, see PCT Application 90/01072 filed Jul. 12, 1990). Such tomatoes can have higher solids contents than conventional tomatoes and produce more tomato paste per unit of fruit weight. The extra lycopene production in such tomatoes is desirable to prevent any lightening of colour that might otherwise be observed in such pastes. Tomatoes containing both types of recombinant construct may be made either by successive transformations, or by crossing two varieties that each contain one of the constructs, and selecting among the progeny for those that contain both.

The invention will now be described further with reference to the accompanying drawings, in FIG. 1 shows the base sequence of the clone pTOM5 (SEQ. ID NO: 2).

The following Examples illustrate aspects of the invention.

EXAMPLE 1

Construction of pTOM5 antisense RNA vectors with the CaMV 35S promoter

Figure 2:
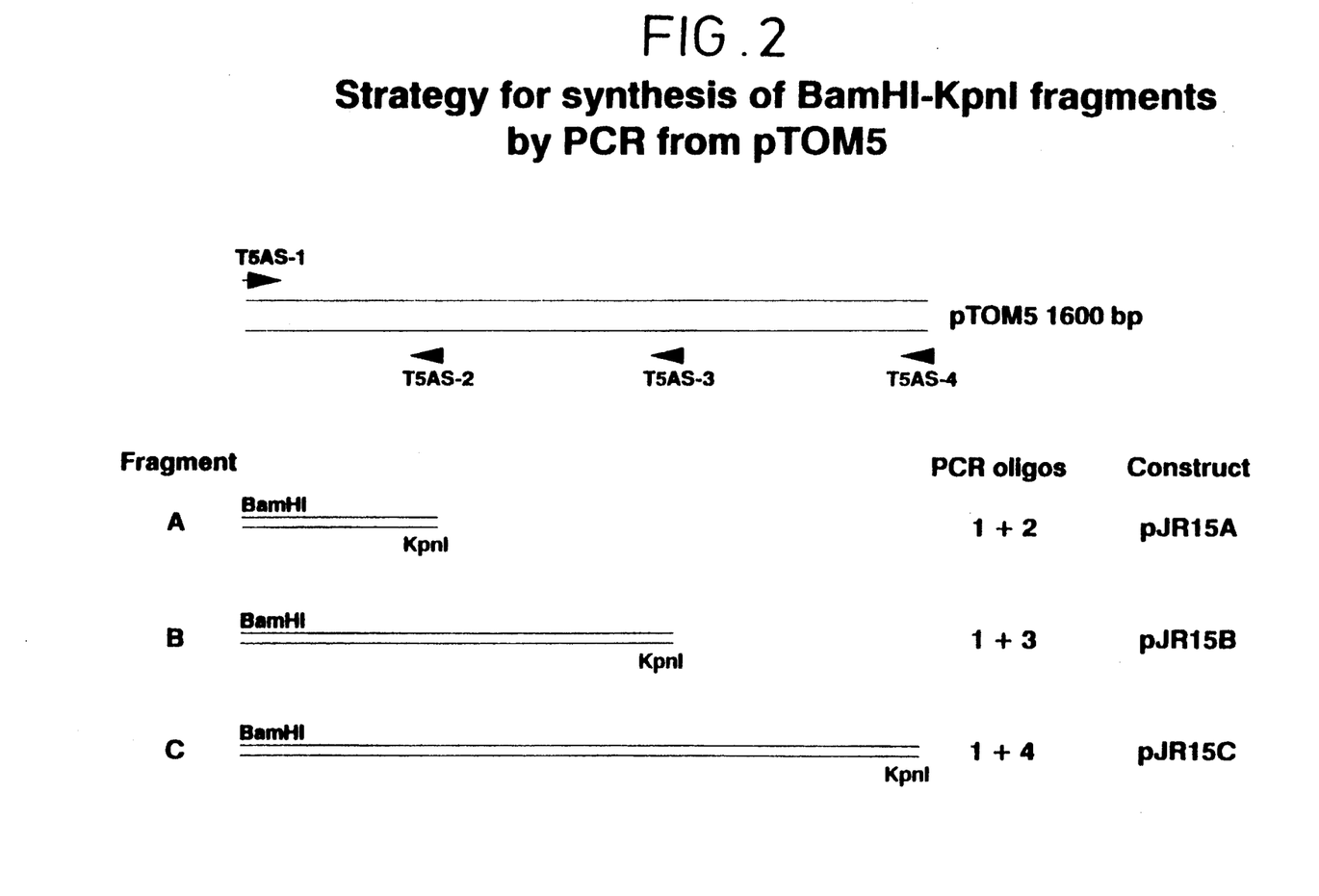
FIG. 2 shows the regions of the pTOM5 sequence which may be synthesized by polymerase chain reaction and used in the construction of vectors according to the invention.

Three vectors may be constructed as shown in FIG. 2 using sequences corresponding to different lengths of the pTOM5 cDNA as shown in FIG. 1.

| 1. bases 1 to 187 | pJR15A |
|---|---|
| 2. bases 1 to 794 | pJR15B |
| 3. bases 1 to 1598 (the complete cDNA) | pJR15C | pJR15B was synthesized in vitro using polymerase chain reactions with synthetic oligonucleotides T5AS-1 and T5AS-3 shown in FIG. 2 as primers and pTOM5 cDNA as template. The synthetic oligo nucleotide primers were designed such that a BamHI restriction site was incorporated at the 5' end a KpnI site was incorporated at the 3' end of the fragment. After cleavage with BamHI and KpnI, the fragment was cloned into the vector pJR1 which had previously been cut with KpnI and BamHI. pJR1 (Smith et al Nature 334, 724–726, 1988) is a Bin19 ( Bevan, Nucleic Acids Research, 12, 8711–8721, 1984) based vector, which permits the expression of the antisense RNA under the control of the CaMV 35S promoter. This vector includes a nopaline synthase (nos) 3' end termination sequence.

After synthesis of the vector pJR15B, the structures and orientation of the pTOM5 sequence was confirmed by DNA sequence analysis.

Figure 3:
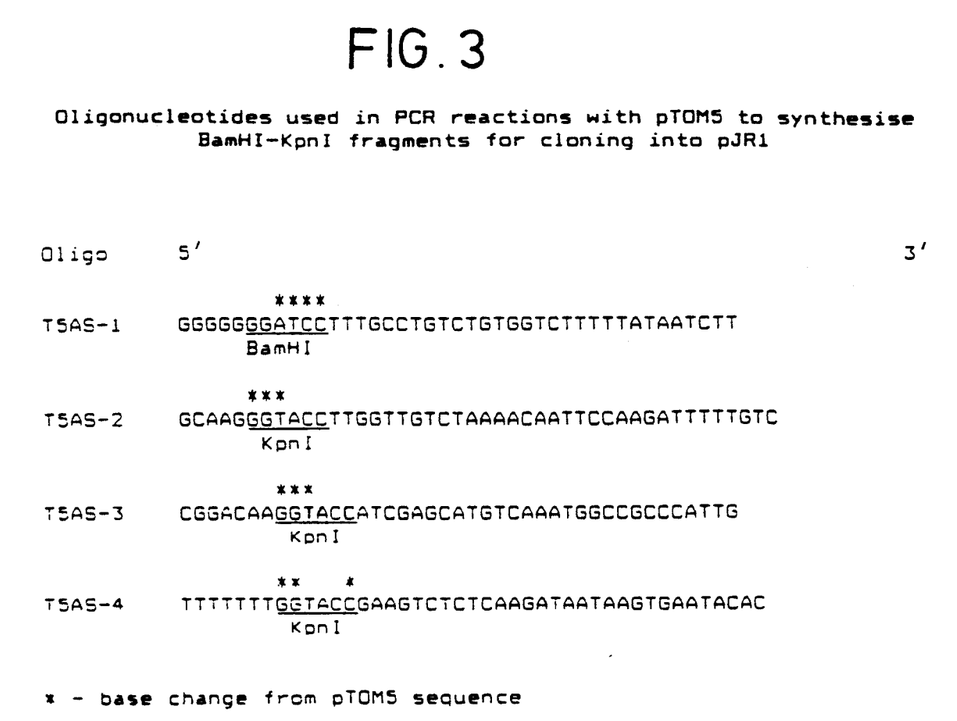
FIG. 3 shows the base sequence of the oligonucleotides used as primers for the polymerase chain reactions to synthesize the fragments illustrated in FIG. 2 (T5AS-1 (SEQ ID NO:3), T5AS-2 (SEQ ID NO: 4), T5AS-3 (SEQ ID NO:5), and T5AS-4(SEQ ID NO: 6))

Vectors pJR15A and pJR15C are made similarly, following the construction schemes shown in FIGS. 2 and 3.

EXAMPLE 2

Construction of pTOM5 antisense RNA vectors with the polygalacturonase promoter.

The fragments of the pTOM5 cDNA described in Example 1 are also cloned into the vector pJR2 to give the following clones:

| 1. bases 1 to 187 | pJR25A |
|---|---|
| 2. bases 1 to 794 | pJR25B |
| 3. bases 1 to 1598 | pJR25C | pJR2 is a Bin19 based vector, which permits the expression of the antisense RNA under the control of the tomato polygalacturonase promoter. This vector includes a nopaline synthase (nos) 3' end termination sequence. This vector does not contain a KpnI or a BamHI site between the promoter and terminator sequences. Consequently, the PCR synthesized fragments are digested with KpnI and BamHI, the cut ends are made flush with T4 polymerase and then cloned into the HincII site of pJR2.

After synthesis, vectors with the correct orientation of pTOM5 sequence are identified by DNA sequence analysis.

EXAMPLE 3

Construction of pTOM5 sense RNA vectors with the CaMV 35S promoter

The fragments of pTOM5 cDNA described in Example 2 are also cloned into the vector pJR1 in the sense orientation to give the following clones:

| 1. bases 1 to 187 | pJR15AS |
|---|---|
| 2. bases 1 to 794 | pJR15BS |
| 3. bases 1 to 1598 | pJR15CS |

The PCR generated fragments are digested with KpnI and BamHI, the cut ends made flush with T4 polymerase and then cloned into the HincII site of pJR1. After synthesis, the vectors with the sense orientation of pTOM5 sequence are identified by DNA sequence analysis.

EXAMPLE 4

Generation and analysis of plants transformed with the vector pJR15B.

The pJR15B vector was transferred to *Agrobacterium tumefaciens* LBA4404 (a micro-organism widely available to plant biotechnologists) and used to transform tomato plants. Transformation of tomato stem segments followed standard protocols (e.g. Bird et al Plant Molecular Biology 11, 651–662, 1988). Transformed plants were identified by their ability to grow on media containing the antibiotic kanamycin. Forty-one individual plants were regenerated and grown to maturity. Thirty-seven of these plants produced fruit which changed colour to yellow rather than to red: they did not turn red even when over-ripe. Fruit from the other four plants turned orange-red.

The flowers of plants with yellow fruit had pale corollae. The accumulation of yellow pigment in flowers varied between individual transformants with some flowers being almost white.

Preliminary analysis indicated that carotenoid accumulation in the yellow fruit was approximately 6% of that in untransformed controls. Almost no lycopene was detected (<2% of that in normal fruit): the majority of residual carotenoid was lutein and β-carotene, neither of which accumulated to significantly greater levels than in the control fruit. Most of the yellow fruit pigment was in the skin, and could not be extracted by methanol. Thus it is unlikely to be carotenoid.

Three of the transformants giving yellow fruit and two of the transformants giving red fruit were submitted to polymerase chain reaction analysis. This indicated that the pJR15B antisense construct was present and intact in all five. DNA blot analysis indicated that the insert copy number was between 1 and 4.

One transformed plant, coded E64C8, with yellow fruit, was selfed to produce progeny. These showed segregation of yellow and white flower colour according to Mendelian principles, indicating that the plant contains one functional copy of the antisense construct, and that the phenotype is stably inherited.

EXAMPLE 5

Construction of pTOM5 expression vectors with the CaMV 35S promoter.

Construction of pJREX5

Figure 7:
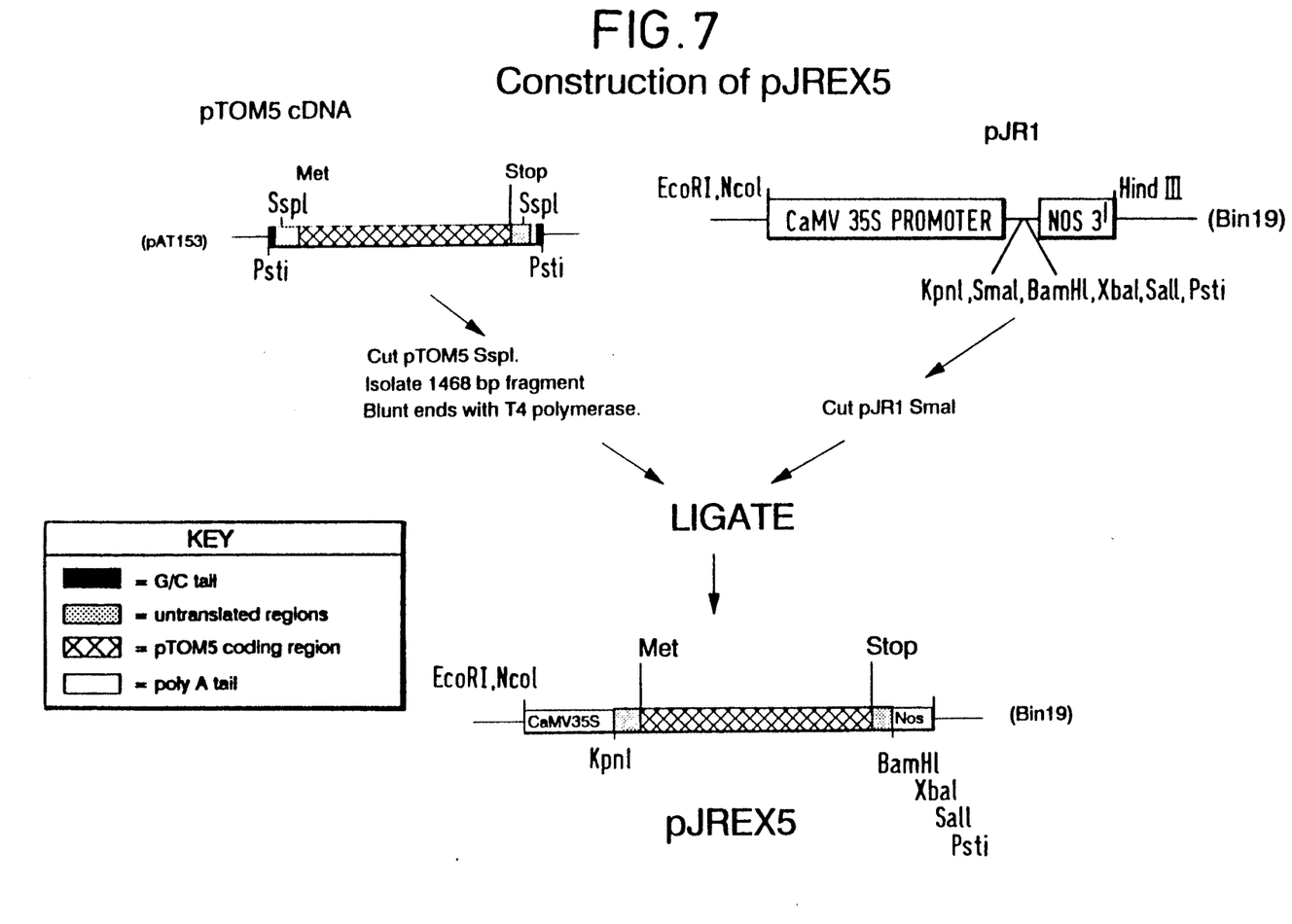
FIG. 7 diagrams the scheme for the manufacture of construct pJREX5.

The expression vector pJREX5 is synthesized in vitro according to the scheme shown in FIG. 7. The 1468 bp SspI fragment is isolated from pTOM5, the cut ends are made flush with T4 polymerase and the resulting product is then cloned into the SmaI site of the plasmid pJR1.

After synthesis, vectors with sense and antisense orientation of the pTOM5 fragment are identified by DNA sequence analysis.

EXAMPLE 6

Construction of pTOM5 expression vectors with the tomato polygalacturonase promoter.

A. Construction of pCB17.

A 1.6 kb region from the 3' end of the tomato PG gene was substituted for the nopaline synthase polyadenylation sequence in pCB1 (Bird et al Plant Molecular Biology 11, 651–662, 1988).

The 5.8 kb SalI/BamHI fragment adjacent to the right arm of lambda EMBL3 in gTOM23 was cloned into the SalI/BamHI sites of pUC8 to give plasmid pGTOM23.5.8. The 1.6 kb BglII fragment from pGTOM23.5.8 was isolated and cloned into the BamHI site of pUC19. Plasmids with the correct orientation of the 1.6 kb BglII insert contained a 550 bp XbaI/BstEII fragment. One such clone was designated A3/1.

Figure 5:
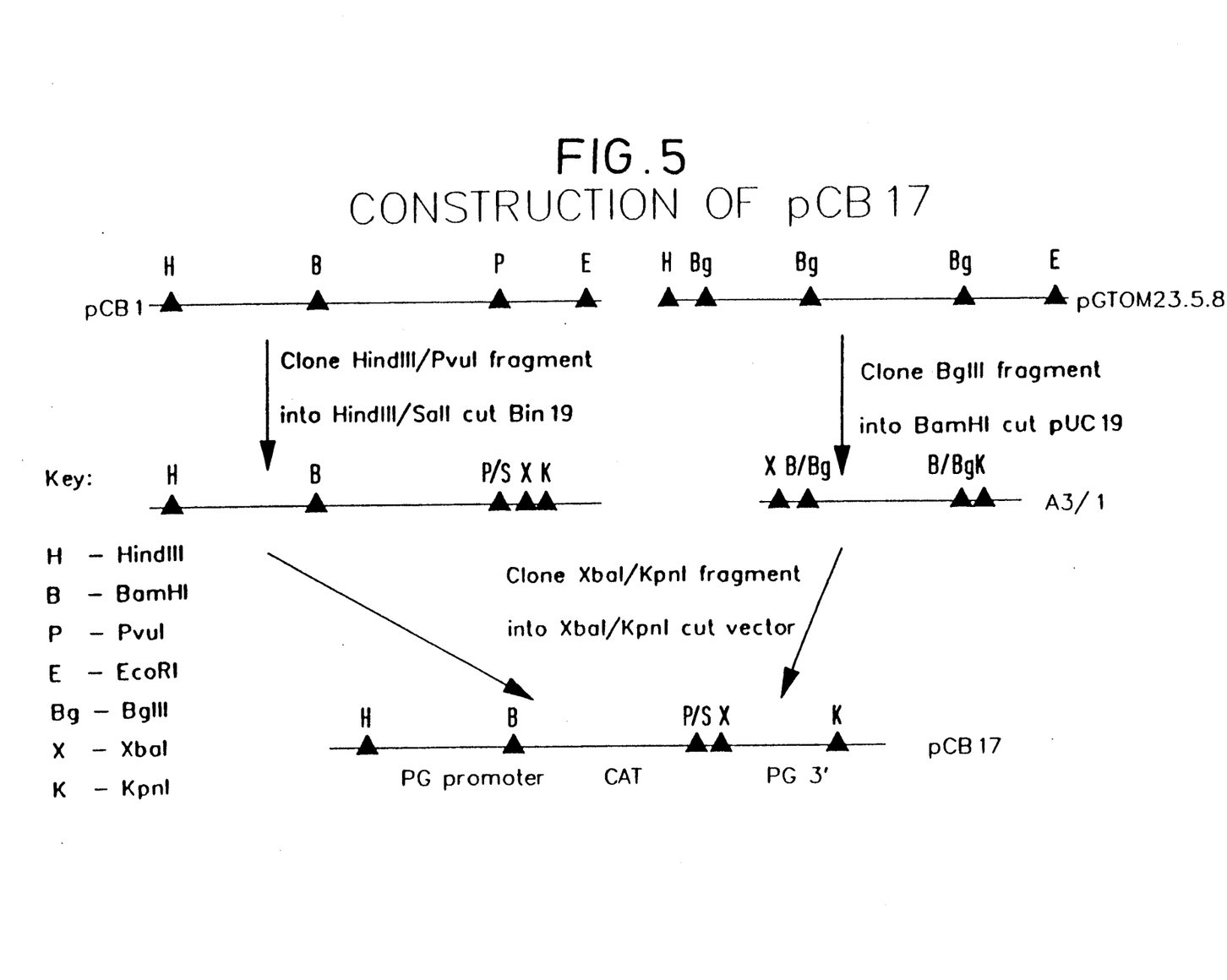
FIG. 5 is a diagram of DNA vector pCB17.

A 2.2 kb HindIII/PvuI was isolated as a fragment from pCB1. This contained a 1.45kb PG promoter fragment and the chloramphenicol acetyl transferase (CAT) gene. This was cloned into Bin19 (Bevan, Nucleic Acids Research, 1984, 12, 8711–8721) which had been cut with SalI followed by filling of the cohesive ends with T4 DNA polymerase and subsequently digested with HindIII. Plasmids with the 2.2 kb HindIII/PvuI fragment contained a 2.2 kb HindIII/XbaI fragment. One of these clones was digested with XbaI and KpnI and ligated with the 1.6 kb XbaI/KpnI fragment from A3/1. After transformation, one clone with the correct insert was designated pCB17 (FIG. 5).

The correct construction of pCB17 was checked by nucleotide sequence analysis of the plasmid DNA at the boundary between the CAT gene and the PG 3' fragment. An unexpected region of the Bin19 polylinker was found to have remained at this junction. This was judged to be unlikely to interfere with the correct functioning of the plasmid. The sequence of pCB17 (SEQ ID NO: 1) in this region is:

```
       CAT              BIN19 POLYLINKER                    PG 3'
...CCGTCCCCGTGCATGCCTGCAGGTCGACTCTAGA GGATCTTCAATATA
       TAG...                            XbaI
```

B. Construction of pCB19

The PG promoter region in plasmid pCB17 was extended by the addition of a 3.5 kb fragment from genomic clone gTOM23 (NCIMB Accession Number 12373).

Figure 6:
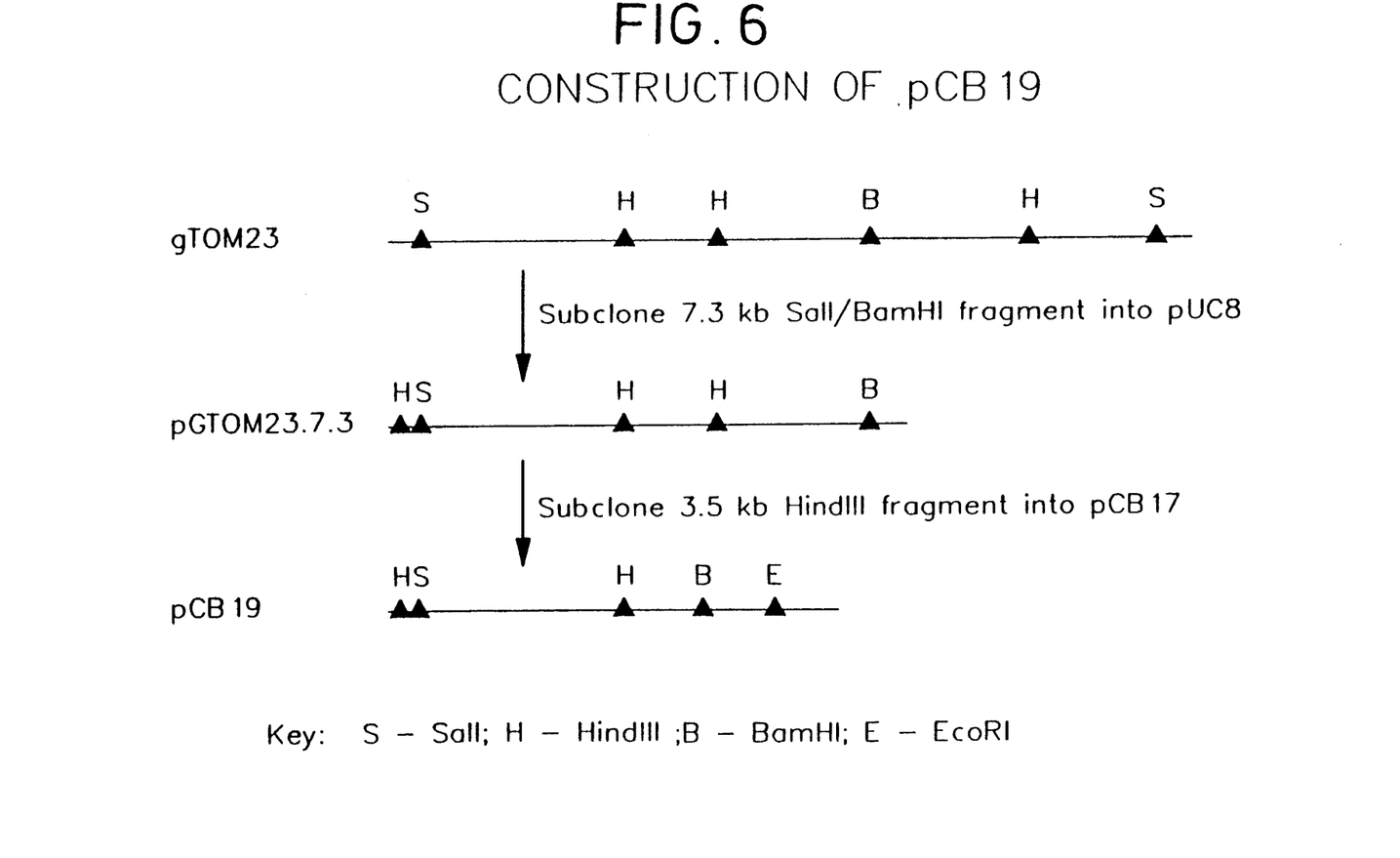
FIG. 6 is a diagram of DNA vector pCB19.

The 3.5 kb HindIII fragment from pGTOM23.7.8 was cloned into the HindIII site in pCB17. Plasmids with the correct orientation of the 3.5 kb Hind AYE insert contained a 4.9 kb SaII/BamI fragment. One such clone was designated pCB19 (FIG. 6).

C. Construction of pCB19

Figure 8:
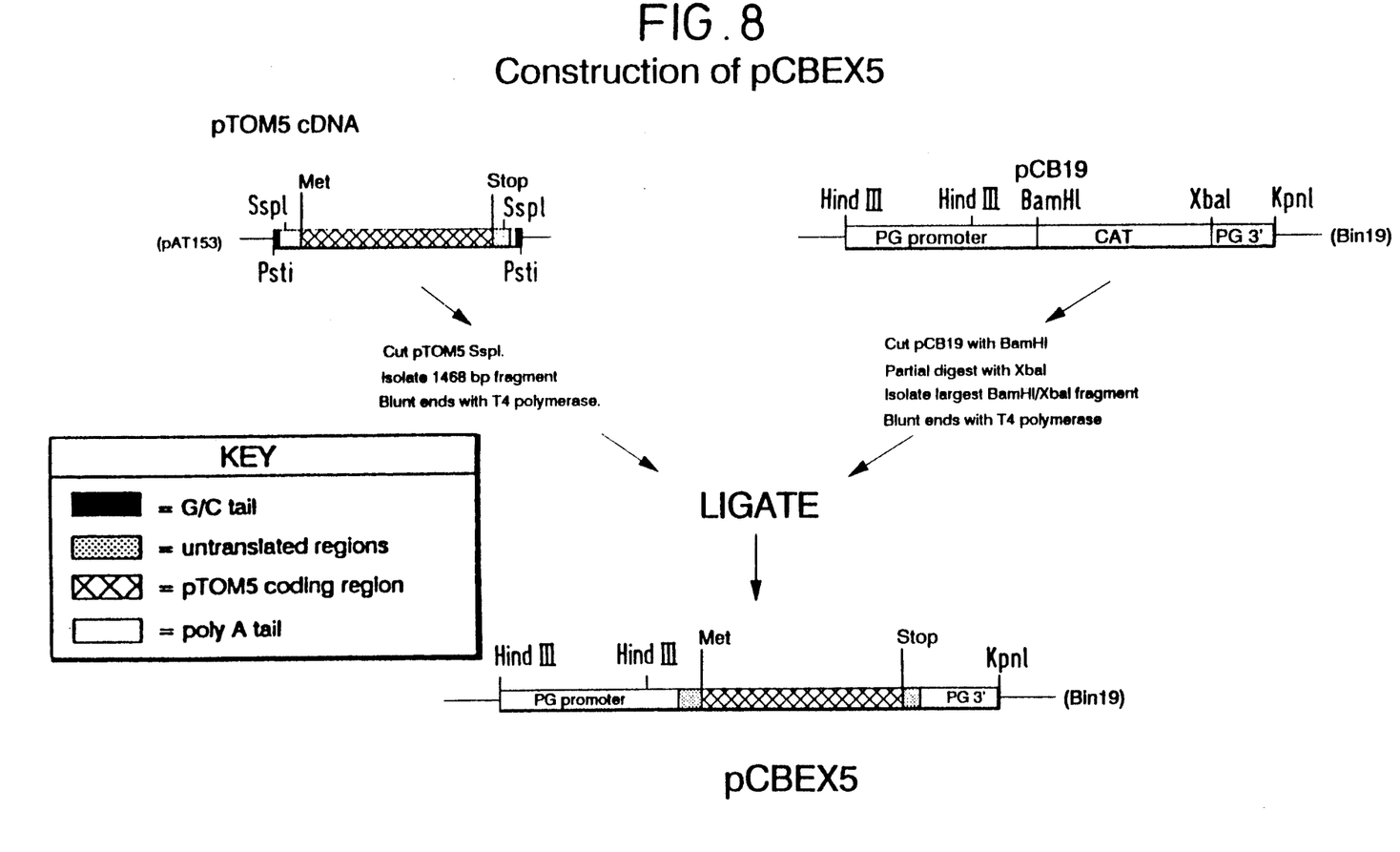
FIG. 8 diagrams the scheme for the manufacture of construct pCBEX5.

The expression vector pCBEX5 is synthesized in vitro according to the scheme shown in FIG. 8. The 1468 bp SspI fragment is isolated from pTOM5, and the cut ends are made flush with T4 polymerase. The resulting product is then cloned into pCB19 from which the BamHI - XbaI fragment encoding chloramphenicol acetyl transferase has been deleted and the cut ends made flush with T4 polymerase.

After synthesis, vectors with sense and antisense orientation of the pTOM5 fragment are identified by DNA sequence analysis.

EXAMPLE 7

Generation of transformed plants with the sense vectors pJREX5 and pCBEX5.

The required sense expression vector (produced in Example 5 or 6) is transferred to *Agrobacterium tumefaciens* LBA4404 (a micro-organism widely available to plant biotechnologists) and used to transform tomato plants. Transformation of tomato stem segments follow standard protocols (e.g. Bird et al Plant Molecular Biology 11, 651–662, 1988). Transformed plants were identified by their ability to grow on media containing the antibiotic kanamycin and by the detection of DNA by DNA blot analysis of their genomic DNA. Ripening fruit are analysed for levels of lycopene and other carotenoids. Plants with higher than normal lycopene levels are selected for further use and study.

---

We claim:

1. A process for modifying the production of carotenoids in tomato plants which comprises transforming such plants with a DNA construct adapted to modify carotenoid biosynthesis, growing such transformed plants or their descendants and selecting tomato plants having plant parts of modified carotenoid content, said construct comprising a DNA sequence encoded by the clone pTOM5, preceded by a transcriptional initiation region operative in plants, so that the construct can generate mRNA in plant cells.

2. A process for producing tomato plants according to claim 1 in which the production of lycopene is modified to produce tomato plants having plant parts of changed colour.

3. A process as claimed in claim 2 in which the plant naturally produces lycopene and the construct is adapted to inhibit the production of lycopene.

4. A process as claimed in claim 2 for producing or intensifying a red colour in plant parts in which the construct is adapted to promote the production of lycopene.

5. A process as claimed in claim 4 in which the construct comprises a transcriptional initiation region operative in plants positioned for transcription of a DNA sequence to give mRNA which can be translated to give the enzyme produced by the gene of pTOM5.

6. A process for modifying the production of carotenoids in tomato plants which comprises transforming such plants with a DNA construct adapted to modify carotenoid biosynthesis, growing such transformed plants or their descendants and selecting tomato plants having plant parts of modified carotenoid content, said construct comprising a transcriptional initiation region operative in plants positioned for transcription of a DNA sequence encoding RNA complementary to mRNA encoding the enzyme produced by the gene of pTOM5.

\* \* \* \* \*